US008595857B2

(12) United States Patent
Donfried et al.

(10) Patent No.: US 8,595,857 B2
(45) Date of Patent: Nov. 26, 2013

(54) PERSONA-BASED IDENTITY MANAGEMENT SYSTEM

(75) Inventors: Paul Andrew Donfried, Richmond, MA (US); Steven T. Archer, Dallas, TX (US); Guy S. Tallent, Jr., New York, NY (US); Ashley Evans, Stonington, CT (US); Peter S. Tippett, Great Falls, VA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 242 days.

(21) Appl. No.: 12/979,820

(22) Filed: Dec. 28, 2010

(65) Prior Publication Data
US 2012/0167234 A1    Jun. 28, 2012

(51) Int. Cl.
*G06F 17/30*    (2006.01)
(52) U.S. Cl.
USPC .................... 726/29; 707/769; 707/E17.014
(58) Field of Classification Search
USPC .................. 726/27–30; 709/769, E17.014
See application file for complete search history.

(56) References Cited

U.S. PATENT DOCUMENTS

| 7,478,157 | B2 * | 1/2009 | Bohrer et al. | 709/226 |
| 7,962,597 | B2 * | 6/2011 | Richardson et al. | 709/223 |
| 8,126,920 | B2 * | 2/2012 | Hu et al. | 707/784 |
| 8,256,013 | B1 * | 8/2012 | Hernacki et al. | 726/28 |
| 8,364,713 | B2 * | 1/2013 | Pollard | 707/784 |
| 2001/0016915 | A1 * | 8/2001 | Sugano et al. | 713/201 |
| 2009/0119222 | A1 * | 5/2009 | O'Neil et al. | 705/76 |
| 2010/0332530 | A1 * | 12/2010 | McKelvie et al. | 707/770 |
| 2012/0054853 | A1 * | 3/2012 | Gupta et al. | 726/17 |

\* cited by examiner

*Primary Examiner* — Amare F Tabor

(57) ABSTRACT

A method, performed by a computer device, may include receiving personal data from a user device associated with personas, where each of the personas corresponds to at least one classification of requesters, associating the received personal data with at least one of the personas, and identifying any of the classifications that correspond to the personas associated with received personal data. The method may further include receiving, from a data requester, a query including a request for the personal data; associating the data requester with a classification; and comparing the classification associated with the data requester to the classifications associated with personal data. The method may further include sending, to the data requester, a message containing the personal data in response to the classification of the data requester corresponding to the classifications of the personal data.

19 Claims, 12 Drawing Sheets

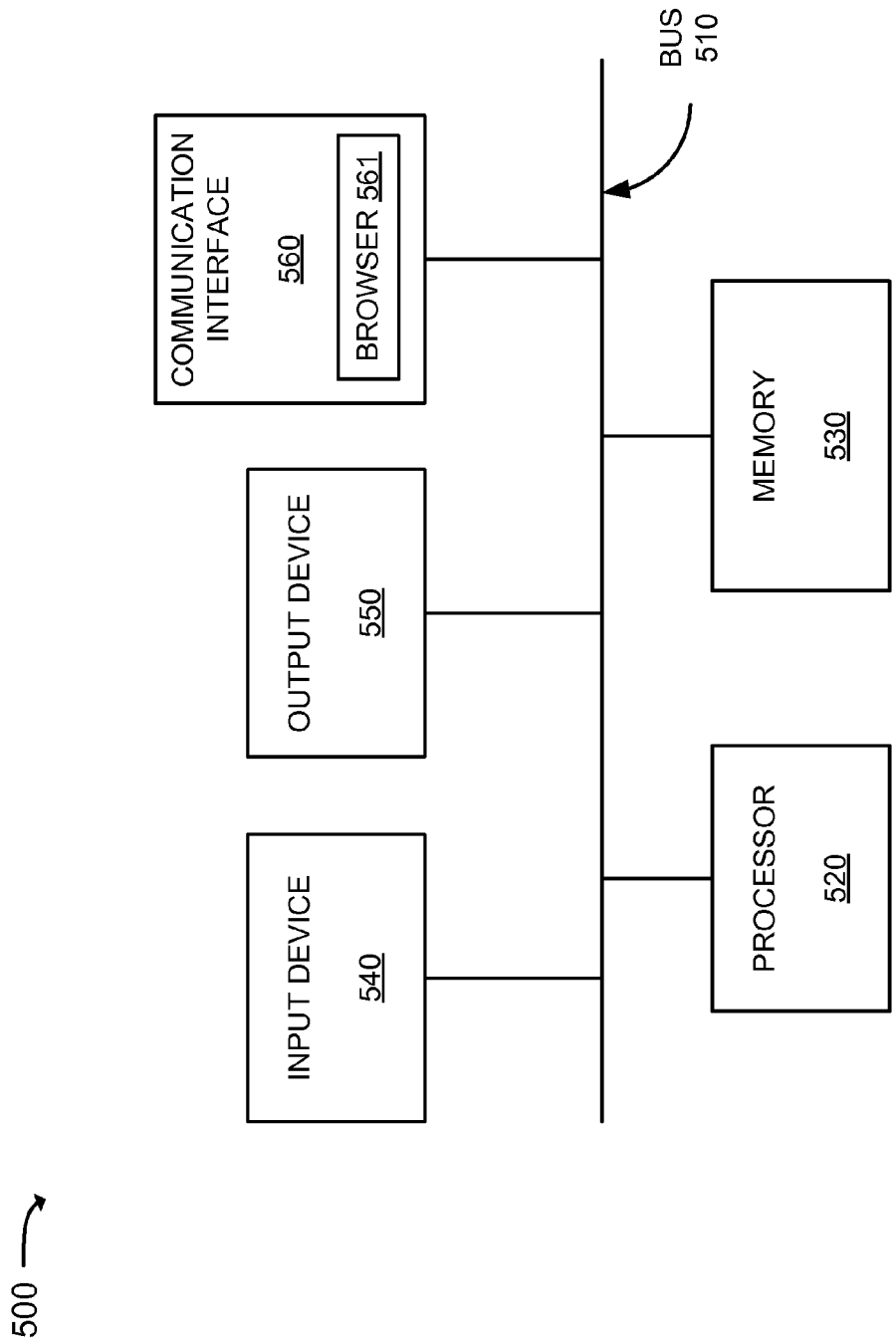

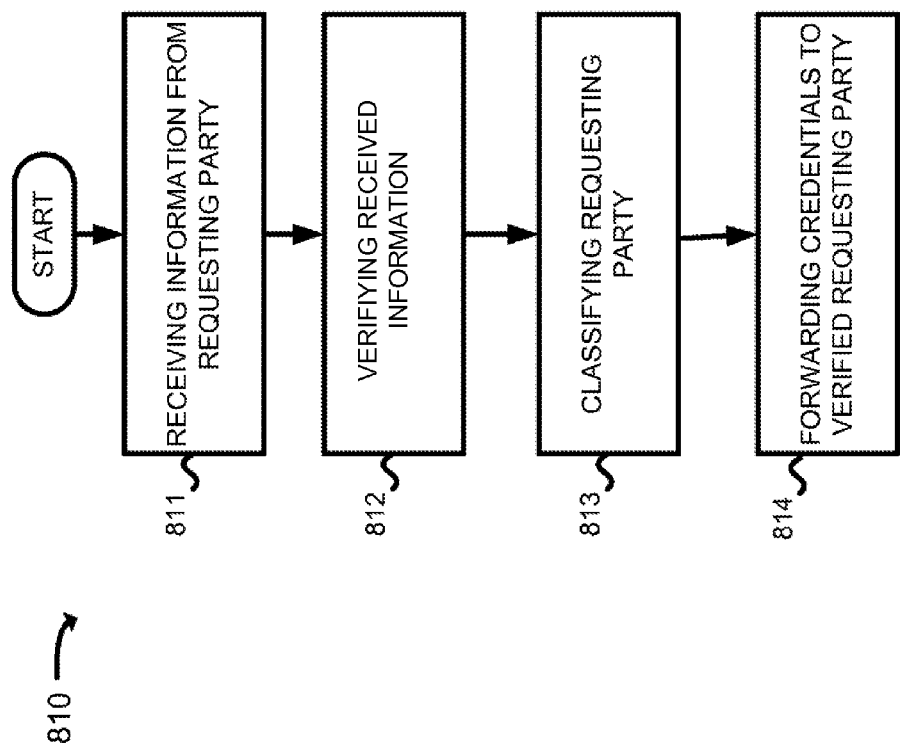

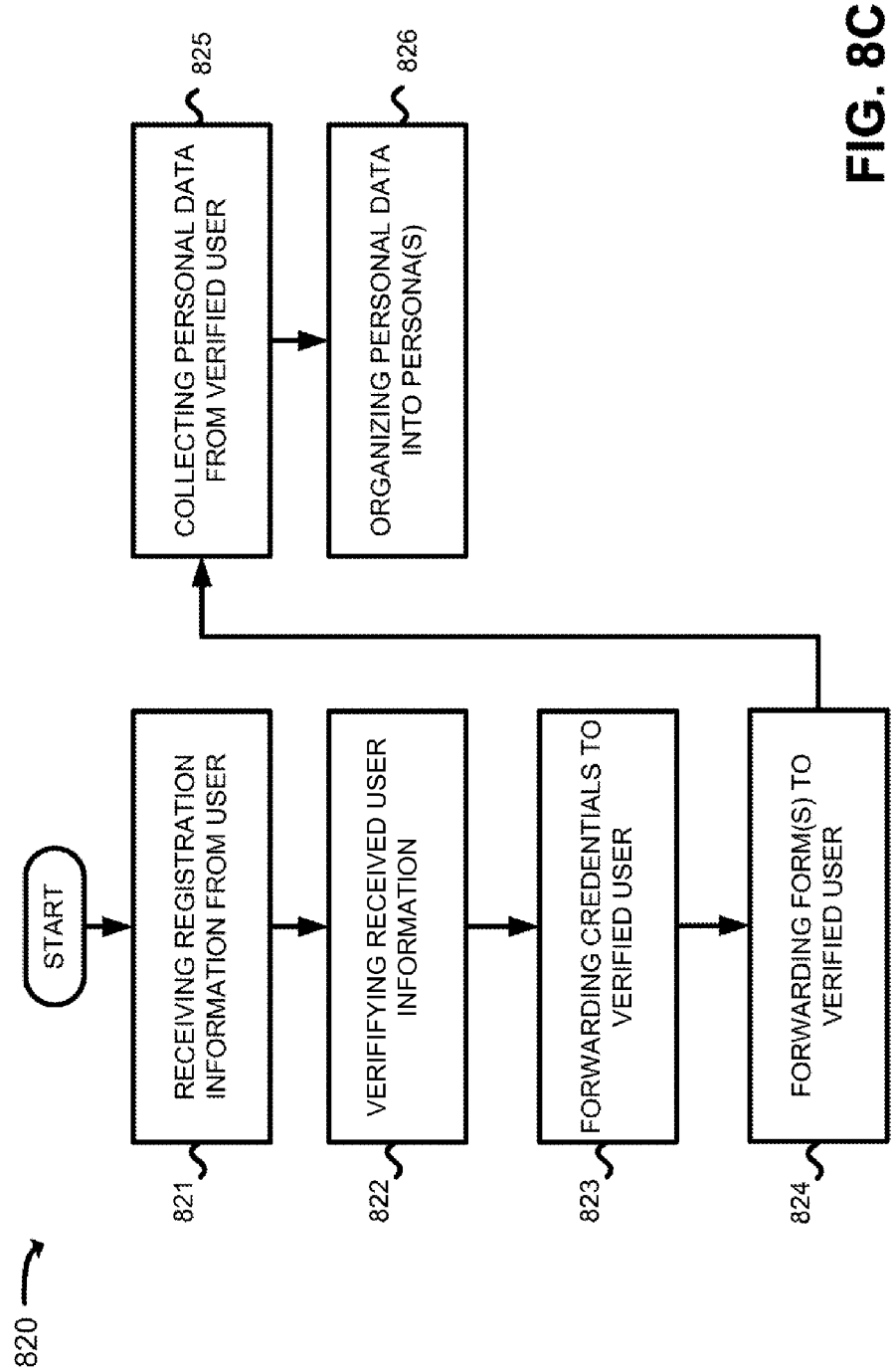

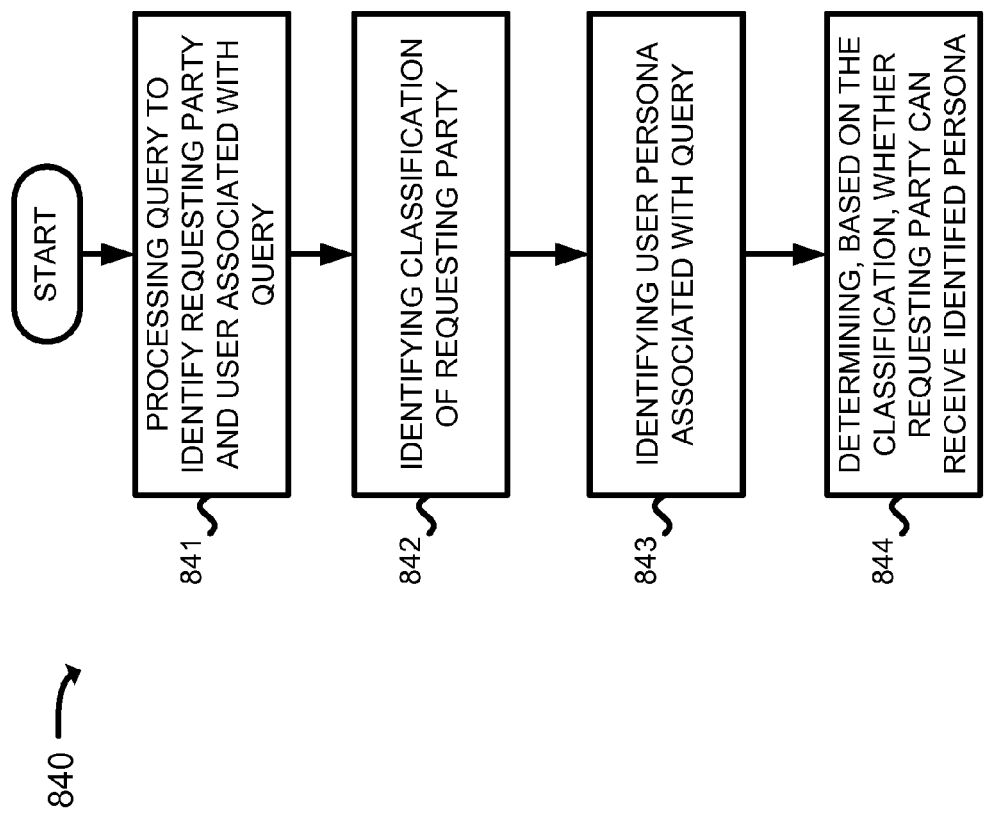

PERSONA-BASED IDENTITY MANAGEMENT SYSTEM

BACKGROUND INFORMATION

In day-to-day interactions with others, an individual typically shares various different details of that individual's personal, financial, and professional information depending on the respective nature of the interactions. For example, an individual may control the dissemination of information by determining a relationship with an intended data recipient and then selecting a persona (or a subset of that individual's information) that is appropriate for the determined relationship. For example, an individual may share certain personal facts, included in a private persona, in interactions with family and friends. Similarly, an individual user controls online dissemination of personal information based on a nature of the individual's interactions with the intended recipients.

BRIEF DESCRIPTION OF THE DRAWINGS

FIG. 5 is a diagram illustrating example components of a computer device included in the system of FIG. 1 according to an implementation described herein;

FIGS. 8A-8D are flow diagrams illustrating a process for persona-based identity management according to an implementation described herein.

DETAILED DESCRIPTION OF PREFERRED EMBODIMENTS

The following detailed description refers to the accompanying drawings. The same reference numbers in different drawings identify the same or similar elements.

An implementation described herein may relate to collecting a user's information and then controlling access to the collected information based on the user's relationship with the requesting party. For example, a user may be registered, and information from that registered user may be collected and sorted to form one or more personas. A requesting entity may be authenticated and classified, and when that entity requests information from the user, that request is processed based on the persona(s) associated with the information request and the classification of the requesting entity.

Figure 1:
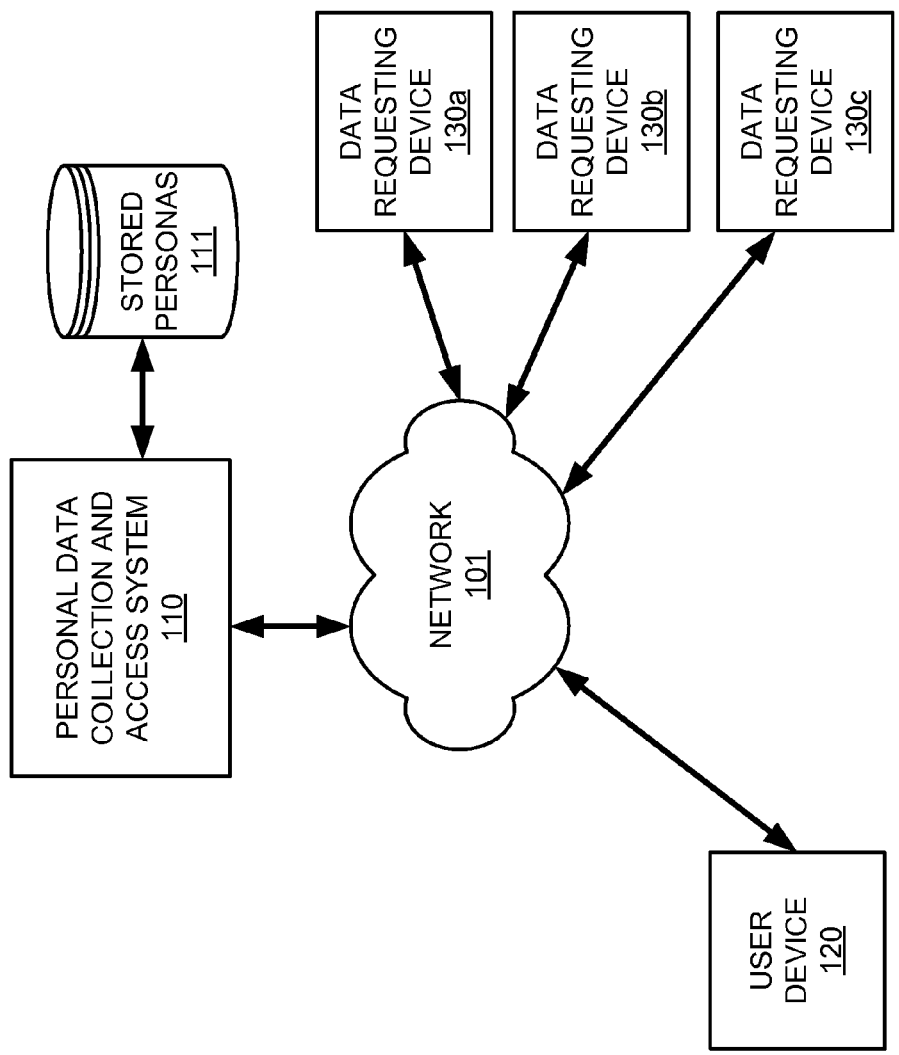
FIG. 1 is a diagram illustrating an example of components of a system according to an implementation described herein.

FIG. 1 is a diagram of a system 100 according to an implementation described herein. As depicted in FIG. 1, system 100 may include personal data collection and access system 110 that stores personas 111, user device 120, and data requesting devices 130a-c (referred to herein collectively as "requesting devices 130" and individually as "requesting device 130"), which are connected by a network 101.

Network 101 may include a circuit-switched network and/or a packet-switched network and may enable components of system 100 to communicate with each other. For example, network 101 may include one or more of a local area network (LAN), a wide area network (WAN), a metropolitan area network (MAN), a wireless network (e.g., a Code Division Multiple Access (CDMA) network, a general packet radio service (GPRS) network, and/or a Long Term Evolution (LTE) network), an ad hoc network, a public switched telephone network (PSTN), a subset of the Internet, any other network, or any combination thereof.

Personal data collection and access system 110 may include one or more devices (e.g., server devices) that interact with user device 120 to register a user associated with user device 120 and to receive personal information, associated with that user. For example, personal data collection and access system 110 may receive identifying information from user device 120, authenticate user device 120 based on the identifying information, receive additional data from user device 120, and provide credentials to user device 120, once it is authenticated. As further described below, personal data collection and access system 110 may further organize the data received from user device 120 into multiple personas 111, with each of the personas 111 being available to a particular classification of data requesting devices 130.

Personal data collection and access system 110 may further include one or more devices that interact with data requesting devices 130 to register respective associated users and/or entities. For example, personal data collection and access system 110 may receive identifying information from data requesting devices 130, authenticate data requesting devices 130 based on the identifying information, and provide respective credentials to authenticated data requesting devices 130. Subsequently, personal data collection and access system 110 may classify data requesting devices 130 and provide, to data requesting devices 130, appropriate information, such as information from one or more of personas 111, based on the classifications.

User device 120 may include any device, associated with a user, capable of exchanging messages with personal data collection and access system 110. User device 120 may include, for example, a mobile communication device, such as a mobile phone, a personal digital assistant (PDA), or a media playing device with communication capabilities; a desktop device, such as a personal computer or a workstation; a laptop computer; a telephone terminal; or any other communication device or combinations thereof. User device 120 may receive messages from personal data collection and access system 110 via a wired (e.g., electrical and/or optical) or a wireless connection.

User device 120 may further be capable of exchanging messages with data requesting devices 130. As part of this messaging between user device 120 and data requesting devices 130, user device 120 may authorize data requesting devices 130 to access one or more of personas 111. For example, user device 120 may provide access credentials to data requesting devices 130 to enable data requesting devices 130 to access one or more of personas 111 through personal data collection and access system 110.

Each of requesting devices 130 may include one or more devices (e.g., server devices) that may exchange messages with personal data collection and access system 110 to authenticate requesting devices 130 and to enable authenticated requesting devices 130 to access one or more of personas 111 stored at personal data collection and access system 110. Each of requesting devices 130 may also include one or more devices that may exchange messages with user device 120 to receive authorization, from user device 120, to access one or more of personas 111 through personal data collection and access system 110.

Although FIG. 1 shows example components of system 100, in other implementations, system 100 may include fewer components, different components, differently arranged components, and/or additional components than those depicted in FIG. 1. Alternatively, or additionally, one or more components of system 100 may perform one or more tasks described as being performed by one or more other components of system 100.

Figure 2:
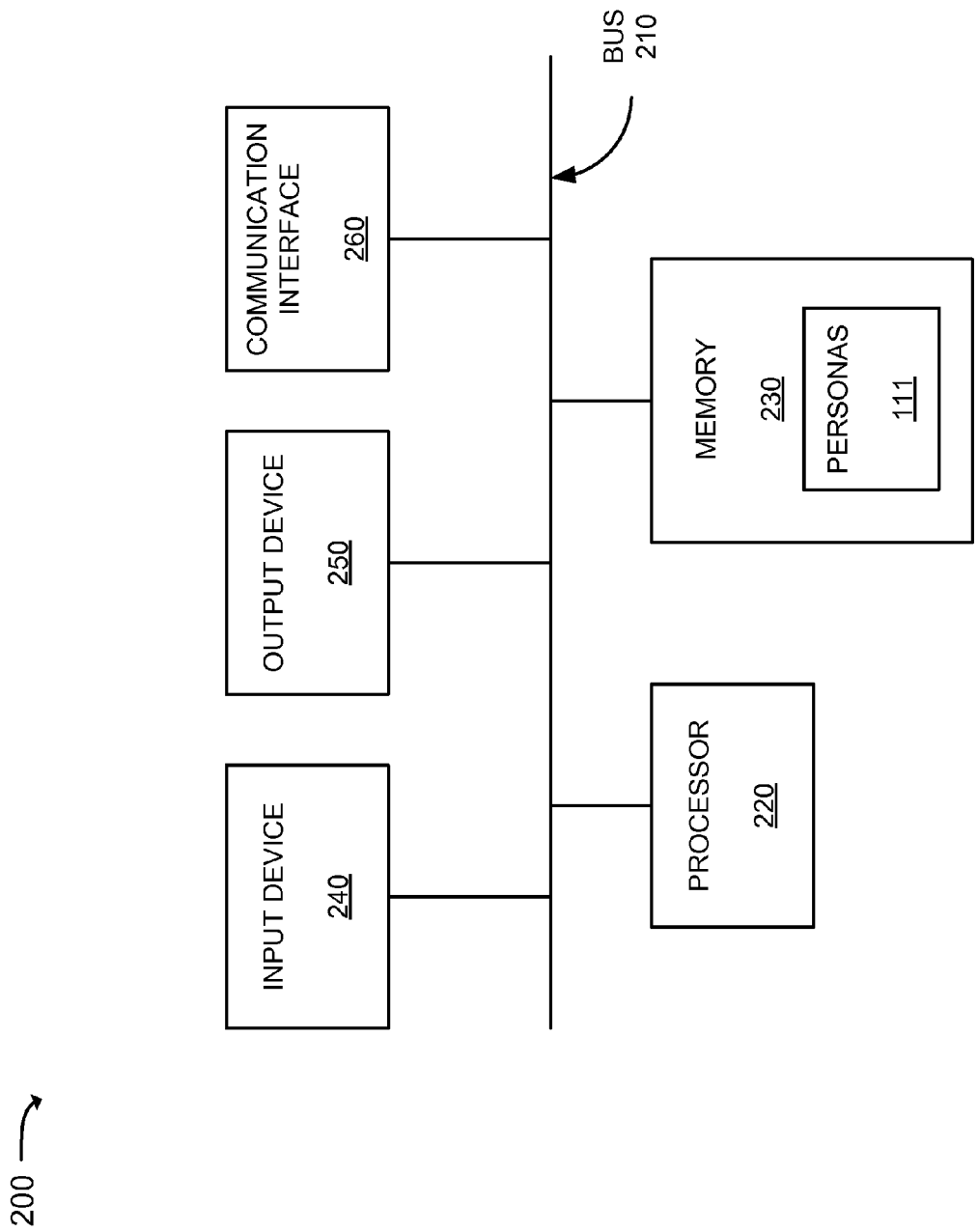
FIG. 2 is a diagram illustrating example components of a personal data collection and access system included in the system of FIG. 1 according to an implementation described herein.

FIG. 2 is a diagram providing example components of personal data collection and access system 110. As shown in FIG. 2, personal data collection and access system 110 may include a bus 210, a processor 220, a memory 230, an input device 240, an output device 250, and a communication interface 260.

Bus 210 may permit communication among the components of personal data collection and access system 110. Processor 220 may include one or more processors, microprocessors, and/or processing logic (e.g., application specific integrated circuits (ASICs) or field programmable gate arrays (FPGAs)) that may interpret and execute instructions.

Memory 230 may include a random access memory (RAM) or another type of dynamic storage device that stores information and instructions for execution by processor 220, a read only memory (ROM) or another type of static storage device that stores static information and instructions for processor 220, and/or some other type of magnetic or optical recording medium and its corresponding drive for storing information and/or instructions.

As described in greater detail below, memory 230 may store, for example, forms that are specified by input device 240 and/or received from another device, such as from data requesting devices 130. Memory 230 may also store, for example, personal data collected from another device, such as personas 111, in response to receiving information from the users that are requested in the forms. Memory 230 may also store, for example, authentication data related to authentication of data providers, such as user device 120, and data requesters such as data requesting devices 130.

Input device 240 may include a device that permits an operator to input information to personal data collection and access system 110, such as a keyboard, a keypad, a mouse, a pen, a microphone, one or more biometric mechanisms, and the like. Output device 250 may include a device that outputs information to the operator, such as one or more light indicators (e.g., light emitting diodes (LEDs)), a display, a speaker, etc.

Communication interface 260 may include any transceiver-like mechanism that enables personal data collection and access system 110 to communicate with other devices and/or systems. For example, communication interface 260 may include mechanisms for communicating with other devices, such as other devices of system 100 through network 101. For example, communication interface 260 may include a modem, a network interface card, and/or a wireless interface card. Communication interface 260 may enable personal data collection and access system 110 to interact with other devices to send forms, from memory 230, to another device, such as user device 120, receive personal information requested in the forms from the other device, and provide controlled access to the received personal information by other devices, such as data requesting devices 130.

As described herein, personal data collection and access system 110 may perform certain operations in response to processor 220 executing software instructions included in a computer-readable medium, such as memory 230. A computer-readable medium may be defined as a non-transitory memory device. A memory device may include memory space within a single physical memory device or spread across multiple physical memory devices. The software instructions may be read into memory 230 from another computer-readable medium or from another device via communication interface 260. The software instructions included in memory 230 may cause processor 220 to perform processes described herein. Alternatively, hardwired circuitry may be used in place of or in combination with software instructions to implement processes described herein. Thus, implementations described herein are not limited to any specific combination of hardware circuitry and software.

Although FIG. 2 shows example components of personal data collection and access system 110, in other implementations, personal data collection and access system 110 may include fewer components, different components, differently arranged components, or additional components than depicted in FIG. 2. Alternatively, or additionally, one or more components of personal data collection and access system 110 may perform one or more tasks described as being performed by one or more other components of personal data collection and access system 110.

Figure 3:
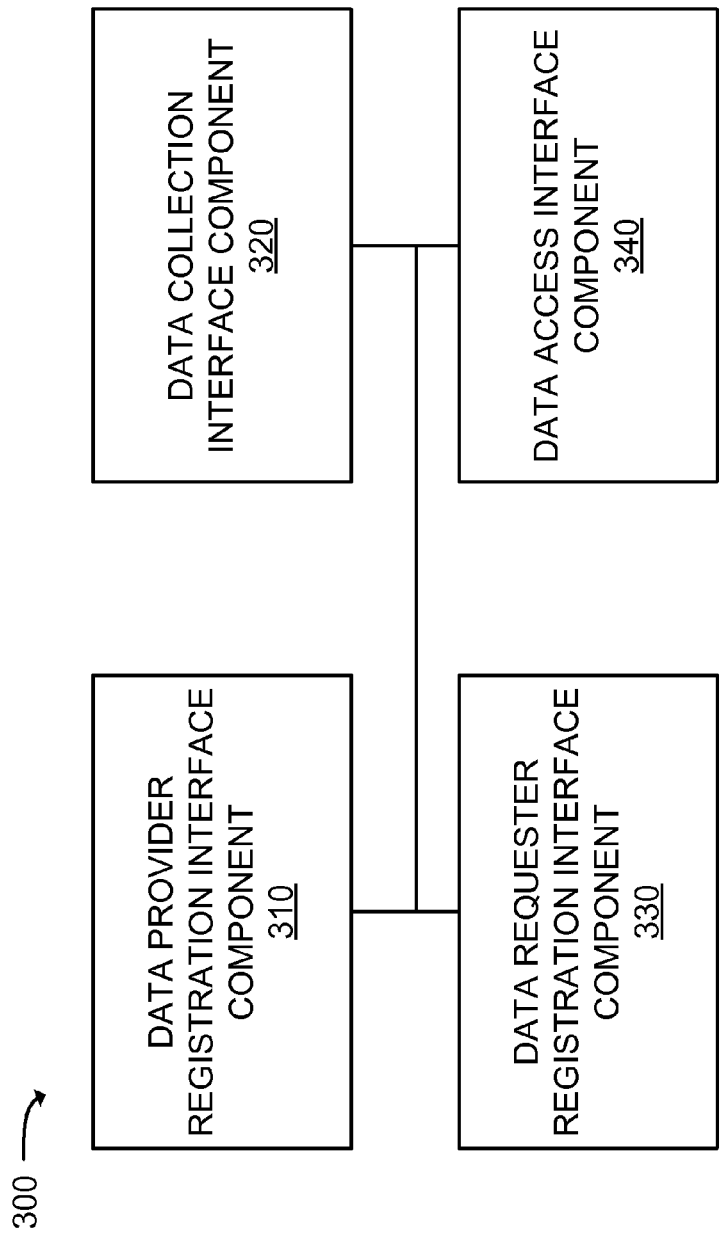
FIG. 3 is a diagram illustrating example functional components of the personal data collection and access system of FIG. 2 according to an implementation described herein.

FIG. 3 is a diagram illustrating functional components of personal data collection and access system 110 according to an implementation described herein. In one implementation, the functions described in connection with FIG. 3 may be performed by one or more components of personal data collection and access system 110 (FIG. 2). As shown in FIG. 3, personal data collection and access system 110 may include data provider registration interface component 310, data collection interface component 320, data requester registration interface component 330, and data access interface component 340.

Data provider registration interface component 310 may receive information from a user, such as a user associated with user device 120. Data provider registration interface component 310 may authenticate the user based on the received information. For example, data provider registration interface component 310 may receive information to identify the user and verify the user's identity using this identifying information. Various types of authentications may be used by data provider registration interface component 310. For example, data provider registration interface component 310 may perform electronic verification that includes a comparison of the received information against stored information associated with the user, such as information previously received from the user or information accessed from publicly available data sources. Other known authentication techniques may be employed by data provider registration interface component 310 to authenticate the user. For example, a user may be screened against lists of criminals. Furthermore, data provider registration interface component 310 may provide the authenticated user with data, such as unique encryption codes or credentials for establishing a secure session or other connection to personal data collection and access system 110.

After data provider registration interface component 310 authenticates the user, data collection interface component

320 may organize the verification information received by data provider registration interface component 310 and/or collect additional information from the authenticated user. For example, data collection interface component 320 may provide to a device associated with an authenticated user, such as user device 120, one or more forms to collect data from the user. As described below, data collection interface component 320 may receive the forms from a device associated with a data requester, such as one of data requesting devices 130. When providing the forms to the device associated to the authenticated user, data collection interface component 320 may pre-populate the forms with previously collected and/or stored data associated with user, such as data acquired from other forms or the information provided by the user to data provider registration interface component 310. Data collection interface component 320 may collect and store the user's responses to the forms.

Figure 4A:
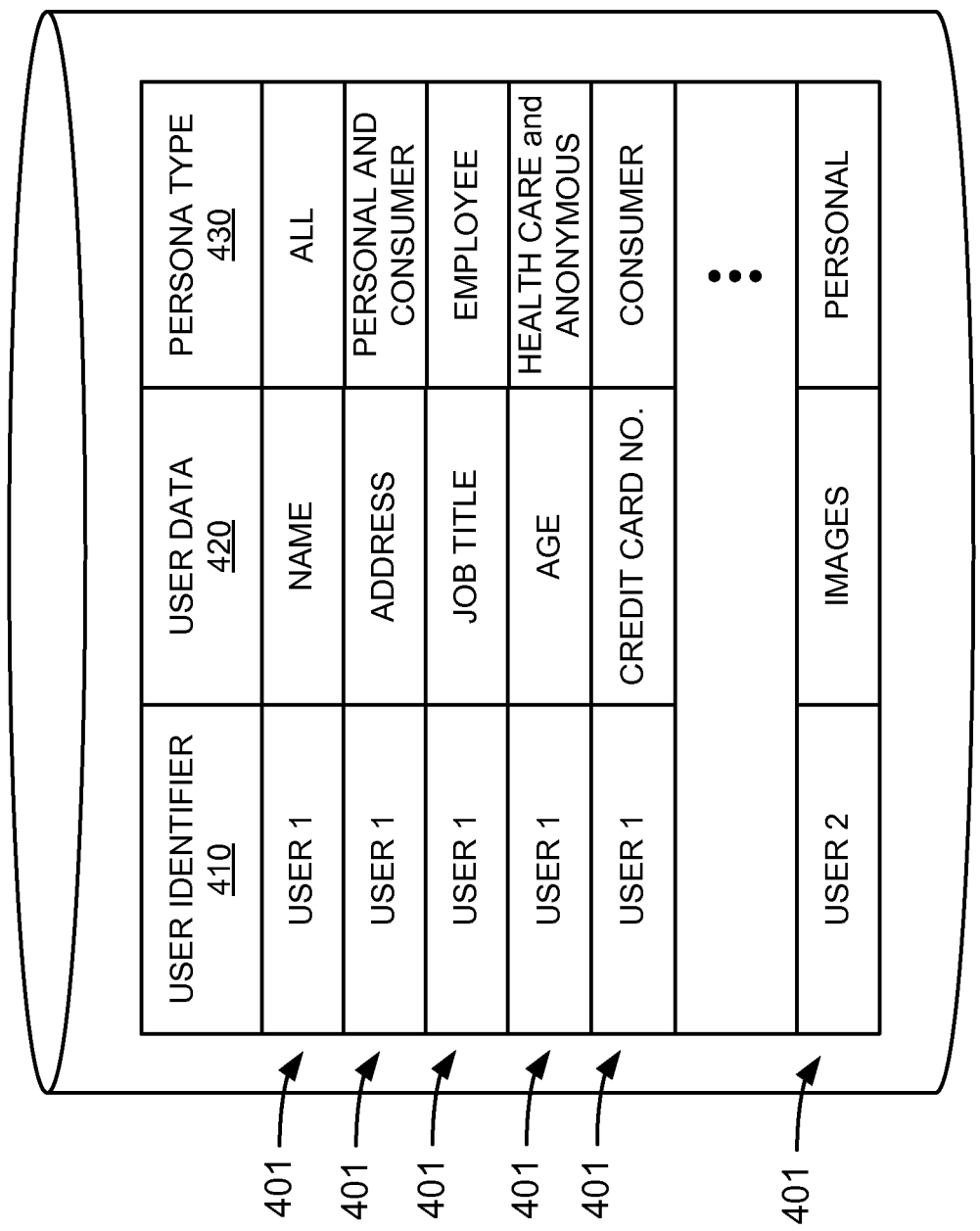
FIG. 4A is a diagram depicting examples of fields that may be stored within one or more personal data record entries by the personal data collection and access system of FIGS. 2 and 3 according to an implementation described herein.

Examples of fields in a database storing the user's personal information are described below with reference to FIG. 4A. As depicted in FIG. 4A, data collection interface component 320 may store one or more personal data record entries 401 (referred to herein collectively as "personal data record entries 401" and individually as "personal data record entry 401"). In one implementation, personal data record entries 401 may be implemented in a storage device included as part of memory 230. It should be appreciated, however, that in other implementations, personal data record entries 401 may be stored in a memory associated with another device or a group of devices, separate from or including memory 230. As shown in FIG. 4A, personal data record entries 401 may include user identification (ID) field 410, user data field 420, and persona type field 430.

User ID field 410 may store an identifier, such as an alphanumeric string, that identifies the particular user (e.g., an authenticated user associated with user device 120). In FIG. 4A, data records 401 are associated with user 1 or user 2. However, personal data record entries 401 may be associated with any number of users.

In one implementation, user ID field 410 stores a user ID that is derived, for example, from the data provided by a user to data provider registration interface component 310 or data collection interface component 320. For example, a user ID, stored in user ID field 410, may be derived from a user's name, address, account information, and/or telephone number. The user ID, stored in user ID field 410, may provide an indication, for example, that two registered users are related or share other personal information, and these relationships may be used to associate or share personal information of two or more registered users. For example, data providers sharing an address may be presumed to be co-workers or family members.

In another implementation, the value stored in user ID field 410 may be derived from or associated with, for example, unique encryption codes or credentials provided by data provider registration interface component 310 to an authenticated user to enable the user to establish a secure connection to personal data collection and access system 110. For example, the value in user ID field 410 may be a portion of the registered user's encryption codes or credentials. Alternatively, the value in user ID field 410 may be functionally-related to encryption code or credential values associated with registered user. For example, a registered user may send information encrypted using en encryption key, and personal data collection and access system 110 may use a complementary value stored in user ID field 410 to decrypt the encoded data. It should be appreciated, however, that these particular types of values for user ID field 410 are provided merely for purposes of example and that other types of values for user ID field 410 may be used.

Continuing with FIG. 4A, personal data record entries 401 may include user data field 420 to store information associated with the user identified in user ID field 410. For example, as depicted in FIG. 4A, examples of information stored in user data field 420 may include a name, address, job title, age, and credit card number. As further depicted in FIG. 4A, user data field may further store data files, such as images. The data stored in user data field 420 may correspond, for example, to data provided by the registered user in response to one or more questions in forms sent from data collection interface component 320. However, these particular types of data stored in user data field 420 are provided merely for purposes of example and other information may be stored in user data field 420. Additionally, or alternatively, user data field 420 may store the actual data provided by the registered user and/or a location (i.e., a pointer or memory address) of the data.

Data collection interface component 320 may organize the data, collected from the authenticated user, to define multiple personas. Data collection interface component 320 may associate information from the user's collected data with the personas, for example, based on inputs from the user. For instance, the user can manually define a persona based on an intended individual or category of individuals to receive particular. Data collection interface component 320 may also organize data from the authenticated user into personas based on one or more forms from which the data was collected. Data collection interface component 320 may also organize data from the authenticated user may into personas based on inputs received from a data requester, such as one of data requesting devices 130a-130c. For instance, a data requester can specify data collected from the user, and data collection interface component 320 can organize the requested data to form a persona that is specific to that data requester.

As depicted in FIG. 4A, personal data record entries 401 may further include persona type field 430 that identifies one or more personas associated with data in user data field 420 of personal data record entries 401. Examples of types of personas that can be included in persona type field 430 may include personal, consumer, employee, healthcare, and anonymous personas. These and other personas are described in greater detail below with respect to FIG. 6. However, these particular examples of personas types stored in persona type field 430 are provided merely for purposes of example and other personas may be stored in persona type field 430.

In another implementation (not depicted), personal data record entries 401 may not include persona type field 430 and, instead, a persona type associated with data entry may be determined by data collection interface component 320 based on information stored in user ID field 410 and user data field 420. For example, a persona type association may be dynamically determined based on various information provided by the registered user or collected by data collection interface component 320 from other data sources. In this way, a persona may be dynamically defined based on a most recent set of information associated with a user and the personal information included in a persona may vary based on various received user input and/or determined conditions. As such, information included in a persona may change, for example, based on detected factors or conditions associated with a user or in response to a request from a data requester. For example, a vendor may request different and/or additional information from a user depending on which particular products are being purchased.

Returning to FIG. 3, data requester registration interface component 330 may receive information from a user/entity associated with one of data requesting devices 130. Data requester registration interface component 330 may authenticate the user/entity based on the received information. For example, data requester registration interface component 330 may receive information to identify the user/entity and to verify the user/entity's identity using this identifying information. Various types of authentications may be used by data requester registration interface component 330. For example, data requester registration interface component 330 may perform electronic verification of the provided information through a comparison of the received information against stored information associated with the user/entity, such as information previously received from the user/entity or information accessed from publicly available data sources. Other known authentication techniques may be employed by data requester registration interface component 330 to authenticate the user/entity.

Figure 4B:
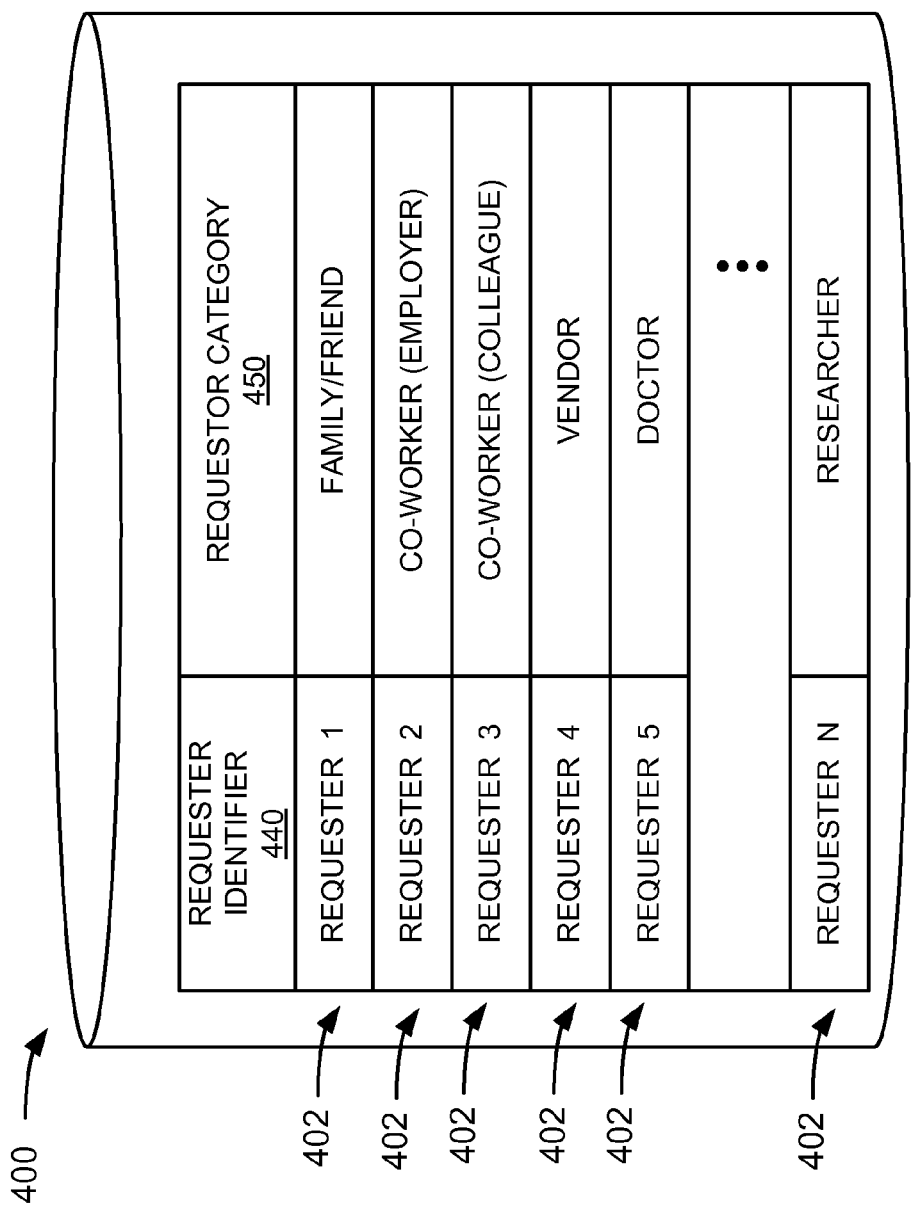
FIG. 4B a diagram depicting examples of fields that may be stored within one or more requester data record entries by the personal data collection and access system of FIGS. 2 and 3 according to an implementation described herein.

Examples of fields in a database storing records of the registered requesters are described with reference to FIG. 4B that depicts one or more requester data record entries 402 (referred to herein collectively as "requester data record entries 402" and individually as "requester data record entry 402") that may be stored by data requester registration interface component 330. In one implementation, requester data record entries 402 may be implemented in a storage device included as part of memory 230. In other implementations, requester data record entries 402 may be stored in a memory associated with another device or a group of devices, separate from or including memory 230. As shown in FIG. 4B, requester data record entries 402 may include requester identification (ID) field 440 and requester category field 450.

Requester ID field 440 may store an identifier, such as an alphanumeric string that uniquely identifies a particular user or entity (e.g., an authenticated user or entity associated with one of data requesting devices 130). In FIG. 4B, requester data record entries 402 are associated with requesters 1-N. It should be appreciated, however, that the particular requester data record entries 402 depicted in FIG. 4b are provided solely for purposes of example, and that requester data record entries 402 may be associated with any number of data requesters.

In one implementation, requester ID field 440 may store a requester ID that is derived, for example, from the data provided by a requester to data requester registration interface component 330. For example, the requester ID, stored in requester ID field 440, may be derived from a data requester's name, address, account information, telephone number, etc. The requester ID, stored in requester ID field 440, may provide an indication, for example, that two registered data requesters are related, and these relationships may be used to categorize the registered requesters. For example, data requesters sharing a contact address may be presumed to be family members or co-workers absent other data collected by data requester registration interface component 330.

In another implementation, the value stored in requester ID field 440 may be derived from or associated with, for example, unique encryption codes or credentials, provided by data requester registration interface component 330 to an authenticated data requester for establishing a secure session or other connection to personal data collection and access system 110. For example, the value in requester ID field 440 may be a portion of the registered requester's encryption codes or credentials. Alternatively, the value in requester ID field 440 may be functionally-related to encryption code or credential values associated with registered data requester. For example, the registered requester may use an assigned encryption code to transmit encrypted, secure data to personal data collection and access system 110, and personal data collection and access system 110 may use a value stored in requester ID field 440 to decrypt the encrypted data. These particular types of values for requester ID field 440 are provided merely for purposes of example, and other types of values for requester ID field 440 may be used.

As part of the registration process, data requester registration interface component 330 may classify a registered data requester into one or more categories. The categories of data collectors may be based on a predicted or defined relationship between the authenticated user providing the data and the authenticated data requester. For instance, data requester registration interface component 330 may classify the data requester based on an analysis of information provided by the user/entity during the registration to discern a relationship between the data requesting entity and the data providing user. Data requester registration interface component 330 may also classify the data requester, for example, based on an input received from the registered user providing the data or from the data requesting user/entity. For example, the registered user may provide, to data requester registration interface component 330, information to designate one or more data requesters as a family member or friend. Likewise, as part of the registration process, a data requester may define a relationship with a user from whom information is requested.

Returning to FIG. 4B, requester data record entry 402 further include requester category field 450 that identifies one or more requester categories associated, by data requester registration interface component 330, with the requester associated with requester ID field 440. FIG. 4B depicts examples of requester categories that include family, friend, co-workers, vendors, doctors, and researcher categories. Each of these categories may further include sub-categories. For example, as depicted in FIG. 4B, the requester category of co-worker may include an employer (or superior) category and a colleague category. Similarly, other co-worker categories may be defined to differentiate between co-workers in different departments, offices, etc. These particular requester categories depicted in requester category field 450 are provided merely for purposes of example, and other types of requester categories may be defined, as appropriate, and stored in requester category field 450.

Continuing with FIG. 3, data access interface component 340 may enable an entity, authenticated by data requester registration interface component 330, to access the personal information collected, from the user, by data collection interface component 320. For example, an authenticated entity may use credentials from data requester registration interface component 330 and/or credentials shared by an authenticated data provider (assigned by data provider registration interface component 310) to access information in one or more personas through data access interface component 340. For example, data access interface component 340 may allow an authenticated data requester to access information associated with user in response that authenticated data requester presenting encryption credentials shared by an authenticated data provider. Furthermore, data access interface component 340 may identify a requester's classification associated with the data requester and provide information from an appropriate one of the personas based on that classification.

Although FIG. 3 shows example functional components of personal data collection and access system 110, in other implementations, personal data collection and access system 110 may include fewer functional components, different functional components, differently arranged functional components, or additional functional components than depicted in FIG. 3. Additionally or alternatively, one or more functional components of personal data collection and access system 110 may perform one or more tasks described as being performed by one or more other functional components of personal data collection and access system 110.

Although FIG. 4A shows examples of fields that may be stored in personal data record entries 401, in other implementations, personal data record entries 401 may include fewer fields, different fields, differently arranged fields, and/or additional fields than depicted in FIG. 4A. Similarly, although FIG. 4B shows examples of fields that may be stored in requester data record entries 402, in other implementations, requester data record entries 402 may include fewer fields, different fields, differently arranged fields, and/or additional fields than depicted in FIG. 4B.

FIG. 5 is a diagram providing examples of components in a computer device 500 that may correspond to user device 120 or one of data requesting devices 130 described above. As shown in FIG. 5, computer device 500 may include a bus 510, a processor 520, a memory 530, an input device 540, an output device 550, and a communication interface 560.

Bus 510 may permit communication among the components of computer device 500. Processor 520 may include one or more processors, microprocessors, and/or processing logic (e.g., application specific integrated circuits (ASICs) or field programmable gate arrays (FPGAs)) that may interpret and execute instructions.

Memory 530 may include a random access memory (RAM) or another type of dynamic storage device that stores information and instructions for execution by processor 520, a read only memory (ROM) or another type of static storage device that stores static information and instructions for processor 520, and/or some other type of magnetic or optical recording medium and its corresponding drive for storing information and/or instructions.

Memory 530 may store, for example, forms received from personal data collection and access system 110 and personal data provide by a user in response to the forms. Memory 530 may also store, for example, authentication data related to authentication of the computer device 500 by personal data collection and access system 110.

Input device 540 may include a device that permits an operator to input information to computer device 500, such as a keyboard, a keypad, a mouse, a pen, a microphone, one or more biometric mechanisms, and the like. Output device 550 may include a device that outputs information to the operator, such as one or more light indicators (e.g., light emitting diodes (LEDs)), a display, a speaker, etc.

Communication interface 560 may also include any transceiver-like mechanism that enables computer device 500 to communicate with other devices and/or systems. For example, communication interface 560 may include mechanisms for communicating with other devices, such as other devices of system 100 through network 101. For example, communication interface 560 may include a modem, a network interface card, and/or a wireless interface card. Communication interface 560 may enable computer device 500 to interact with other devices to receive forms and forward a user's responses to forms to another device, such as personal data collection and access system 110, and to provide authorization to enable other devices, such as data requesting devices 130, to access to the stored personal information specified by a user associated with computer device 500.

Communications interface 560 may further include a browser 561 or another application to receive a form from data requesting devices 130, to receive a user input in response to the form, and to forward the user's inputs to personal data collection and access system 110. Alternatively, browser 561 may enable a data requesting user to create and forward a form to personal data collection and access system 110.

As described herein, computer device 500 may perform certain operations in response to processor 520 executing software instructions included in a computer-readable medium, such as memory 530. The software instructions may be read into memory 530 from another computer-readable medium or from another device via communication interface 560. The software instructions included in memory 530 may cause processor 520 to perform processes described herein. Alternatively, hardwired circuitry may be used in place of or in combination with software instructions to implement processes described herein. Thus, implementations described herein are not limited to any specific combination of hardware circuitry and software.

Although FIG. 5 shows examples of components of computer device 500, in other implementations, computer device 500 may include fewer components, different components, differently arranged components, or additional components than depicted in FIG. 5. Alternatively, or additionally, one or more components of computer device 500 may perform one or more tasks described as being performed by one or more other components of computer device 500.

Figure 6:
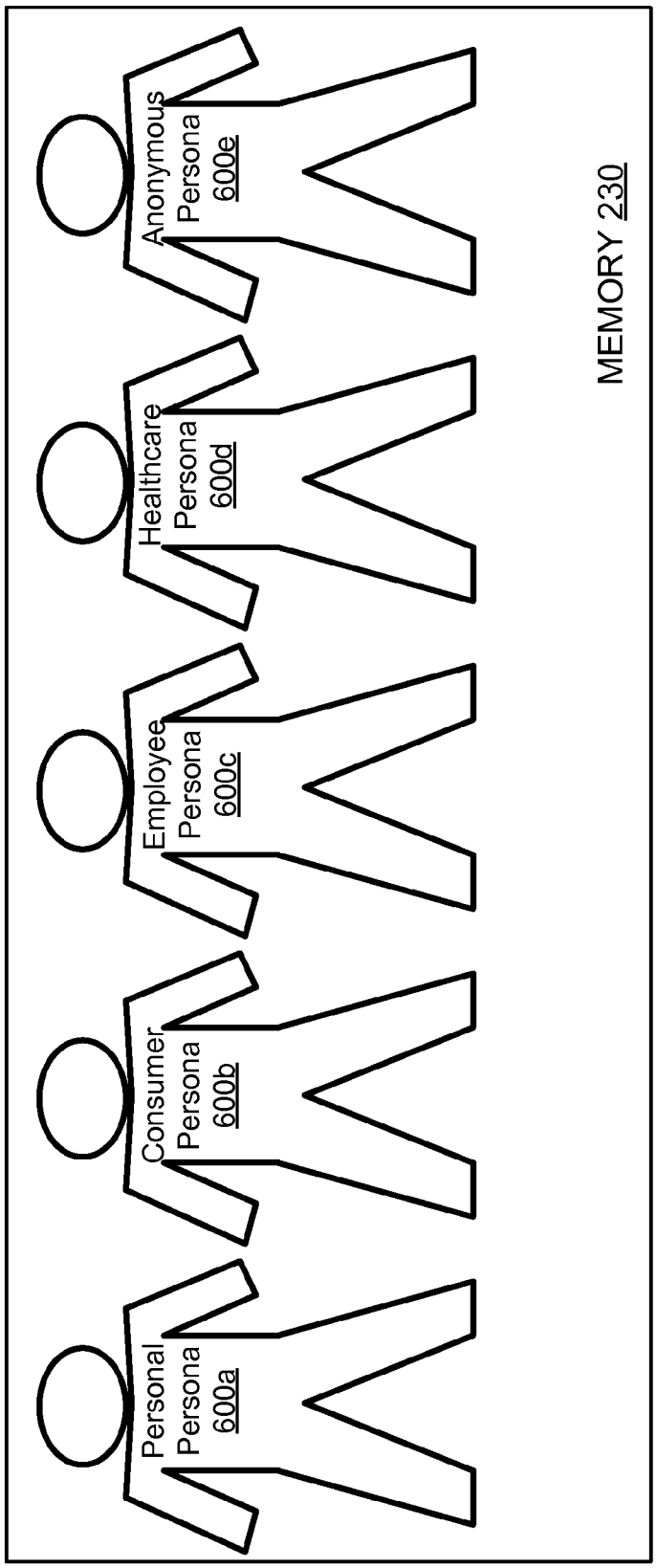
FIG. 6 a diagram depicting examples of personas that may be stored by the personal data collection and access system of FIGS. 2 and 3 according to an implementation described herein.

FIG. 6 depicts examples of personas 600a-e for a registered user that may be stored in connection with the operation of data access interface component 340. In one implementation, personas 600a-e may be implemented in a storage device included as part of memory 230. It should be appreciated, however, that in other implementations, personas 600a-e may be stored in a memory associated with another device or a group of devices, separate from or including memory 230. As described above, various components of personal data collection and access system 110 may sort personal collected data into one or more personas, categorize data requesters into one or more categories, and then provide information associated with one of the personas to a requester based on that's requester's category.

As described above, a person (or a biological entity) may be associated with multiple personas. As used herein, a persona includes a set of identity attributes associated with a biological entity, with each persona including one or more core attributes. FIG. 6 depicts that a user is associated, for example, with personal persona 600a, consumer persona 600b, employee persona 600c, healthcare persona 600d, and anonymous persona 600e. Personal persona 600a may be shared, by data access interface component 340, with data requesters that are classified, for example, as friends, family, and/or other close acquaintances, and the core attributes included in the personal persona may include, for example, personal information about the user and the user's family and other personal data, such as personal images.

Consumer persona 600b may be shared, by data access interface component 340, with data requesters that are classified, for example, as vendors. Core attributes included in the consumer persona 600b may include, for example, the user's address and payment information. It should be appreciated, however, that sub-personas may be generated as needed by the registered users and data requesters. For example, a user may be associated with multiple consumer personas, such as a mail-order consumer persona to receive products to the user's home, a business consumer persona to receive products to the user's workplace, and a personal services persona to receive services at an appropriate location. Similarly, a sub-persona may be associated with a particular vender such that personal information required for transaction with that vendor may be included in the persona and available for access by the vender. For example, a car rental company may require personal information (e.g., driver's license number, insurance policy number, age, etc.) that may not be needed by other types of vendors. To meet the specific needs, a vender may provide information to the personal data collection and access system 110 to define a sub-persona that contains specific information.

Employee persona 600c may be shared, by data access interface component 340, with data requesters that are classified, for example, as co-workers or an employer. Core attributes included in the employee persona 600c may include, for example, the user's work address, work calendar, work contacts, education and work history, details, etc. Other information meaningful to an employer relationship may be included in employee persona 600c. For example, employee persona 600c may be used to share work-related information, such as identification of co-workers within a particular department, a status of a work project, or contact information for work associates and/or customers.

Healthcare persona 600d may be shared, by data access interface component 340, with data requesters that are classified, for example, as patients (when the user is identified as a healthcare provider) or a doctor (when the user is identified as a patient). The core attributes included in healthcare persona 600d may include, for example, an indication of the user's role in healthcare (e.g., whether the user is a healthcare provider or a patient), healthcare information shared between the user and doctor, etc. For example, the healthcare persona 600d may include information about the user's health or indicate a computer network address where this information can be acquired. Again, it should be appreciated that various sub-personas may be defined as needed by the data requesters.

Anonymous persona 600e may allow a user to register anonymously with personal data collection and access system 110 such that the certain identifying information associated with the user is not included in the anonymous persona 600e. For example, anonymous persona 600e may include enough information to allow the user to finish a transaction, without providing unnecessary aspects of the user's personal information. In this way, anonymous persona 600e enables, for example, a vendor can have confidence that received personal information, such as payment information, is reliable without identifying the user. It should be appreciated that some data requesters may accept anonymous persona 600e while other data requesters may request additional details about the user as needed to complete a commercial transaction.

Also, while FIG. 6 depicts examples of personas formed from user data, fewer personas, different personas, differently arranged personas, and/or additional personas than depicted in FIG. 6 may be used in implementations of the present application.

Figure 7:
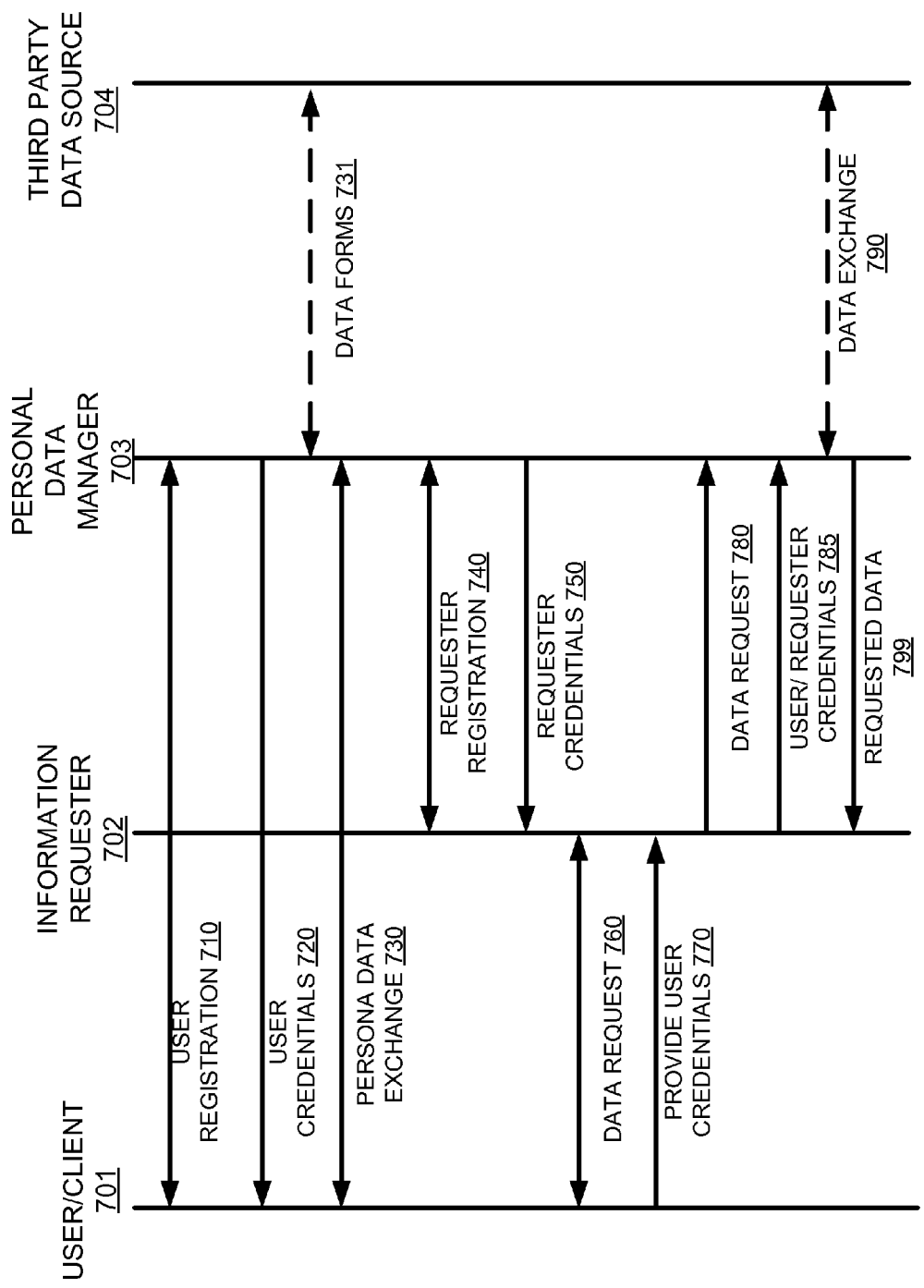
FIG. 7 is a diagram illustrating an example signal flow according to an implementation described herein.

FIG. 7 is a diagram illustrating an example of signal flows, according to an implementation described herein, that may be between one or more of user/client 701 (that may correspond to user device 120, information requester 702 (that may correspond to requesting devices 130), and personal data manager 703 (that may correspond to personal data collection and access system 110). According to an implementation described herein, the signal flows depicted in FIG. 7 may further include signals from third-party data source 704.

User/client 701 may exchange one or more user registration signals 710 with personal data manager 703. For example, as described above with respect to user device 120, user registration signals 710 may include user/client 701 providing authentication data to personal data manager 703, and personal data manager 703 using this information to authenticate user/client 701.

Once authenticated, user/client 701 may receive user credentials signal 720 from personal data manager 703. User credentials signal 720 may include credentials or encryption data that user/client 701 may use to authenticate information sent to personal data manager 703. For example, user credentials signal 720 may include a digital signature or other known encryption key value that personal data manager 703 may use to verify that information from user/client 701 is genuine and reliable.

For example, as part of personal data exchange signals 730, user/client 701 may receive one or more forms from personal data manager 703, and provide the data requested in the received forms in a response to the personal data manager 703. User/client 701 may use data provided in user credentials signal 720 to mark the reply data requested by the forms an included in one or more of personal data exchange signals 730. Personal data manager 703, when receiving the reply to the form(s) from user/client 701, may use the data in user credentials signal 720 to authenticate the received data from user/client 701, such as to decrypt the data using information provided by personal data manager 703 in user credentials signal 720.

One or more of the forms transmitted by personal data manager 703 in personal data exchange signals 730 may optionally be received from data source 704 in data forms signal 731. For example, data source 704 may be an external data repository that stores and provides the forms. Alternatively, data source 704 may be associated with information requester 702.

Information requester 702 may exchange one or more requester registration signals 740 with personal data manager 703. For example, personal data manager 703 may request, through requester registration signals 740, information from information requester 702, and information requester 702 may provide this authentication data to personal data manager 703. Personal data manager 703 may use this information to authenticate information requester 702.

After registration through requester registration signals 740, personal data manager 703 may provide requester credentials signal 750 to information requester 702. Requester credentials signal 750 may include credentials or encryption data that information requester 702 may use to authenticate another signal information sent to personal data manager 703. For example, requester credentials signal 750 may include a digital signature or another known encryption data value that personal data manager 703 may use to verify that other signals, such as a data request, from information requester 702 are genuine and reliable.

Continuing with FIG. 7, a series of signals for information requester 702 to acquire information from personal data manager 703 are now described. For example, data collection by information requester 702 may be initiated by data request signals 760 between user/client 701 and information requester 702. For example, as part of an on-line commercial transaction, user/client 701 may send an invitation or other type of authorization and/or request to information requester 702 to initiate access to data associated with user/client 701 and controlled by personal data manager 703. Similarly, as part of a hospital registration, a patient associated with user/client 701 may authorize information requester 702 associated with the hospital to access the patient's medical records. As part of this authorization included in data request signals 760, user/client 701 may send user credential signals 770 to information requester 702. User credential signals 770 may include data that information requester 702 may use to prove the authenticity of a related data request (data request signals 780) to personal data manager 703.

For example, to access the data stored by personal data manager 703, information requester 702 may send, with data request signals 780, user/requester credentials signal 785 that includes credentials associated with user/client 701 and information requester 702. For example, user/requester credentials signal 785 may include credentials received by user/client 701 in user credentials signals 720 and provided to information requester 702 in user credential signals 770. User/requester credentials signal 785 may further include credentials received by information requester 702 in requester credentials signals 750. Personal data manager 703 may use the information in user/requester credentials signal 785 to verify both that information access is authorized by user/client 701 and that information requester 702 is eligible to access the stored information. Similarly, as described above, personal data manager 703 may determine whether to grant access to information based on one of user/client's persona associated with the requested data and based on classification assigned to information requester 702.

Upon authentication of the information requester 702 based, for example, on user/requester credentials signal 785, personal data manager 703 may locate the requested data. For example, personal data manager 703, in one implementation, may locally store the information received from the user/client 701 in personal data exchange 730. Personal data manager 703 may optionally obtain the requested stored data from data source 704 (data exchange signal 790). Personal data manager 703 may then send the requested data, through requested data signal 799, to information requester 702.

FIGS. 8A-8D are flow diagrams illustrating a persona-based identity management process 800 according to an implementation described herein. In one implementation, persona-based identity management process 800 may be performed by personal data collection and access system 110. In other implementations, some or all of persona-based identity management process 800 may be performed by another device or a group of devices separate from and/or possibly remote from personal data collection and access system 110 and/or including personal data collection and access system 110. In one implementation, persona-based identity management process 800 may be manually initiated by an administrator. In another implementation, persona-based identity management process 800 may be performed automatically (e.g., at particular intervals or in response to particular received data).

Figure 8A:
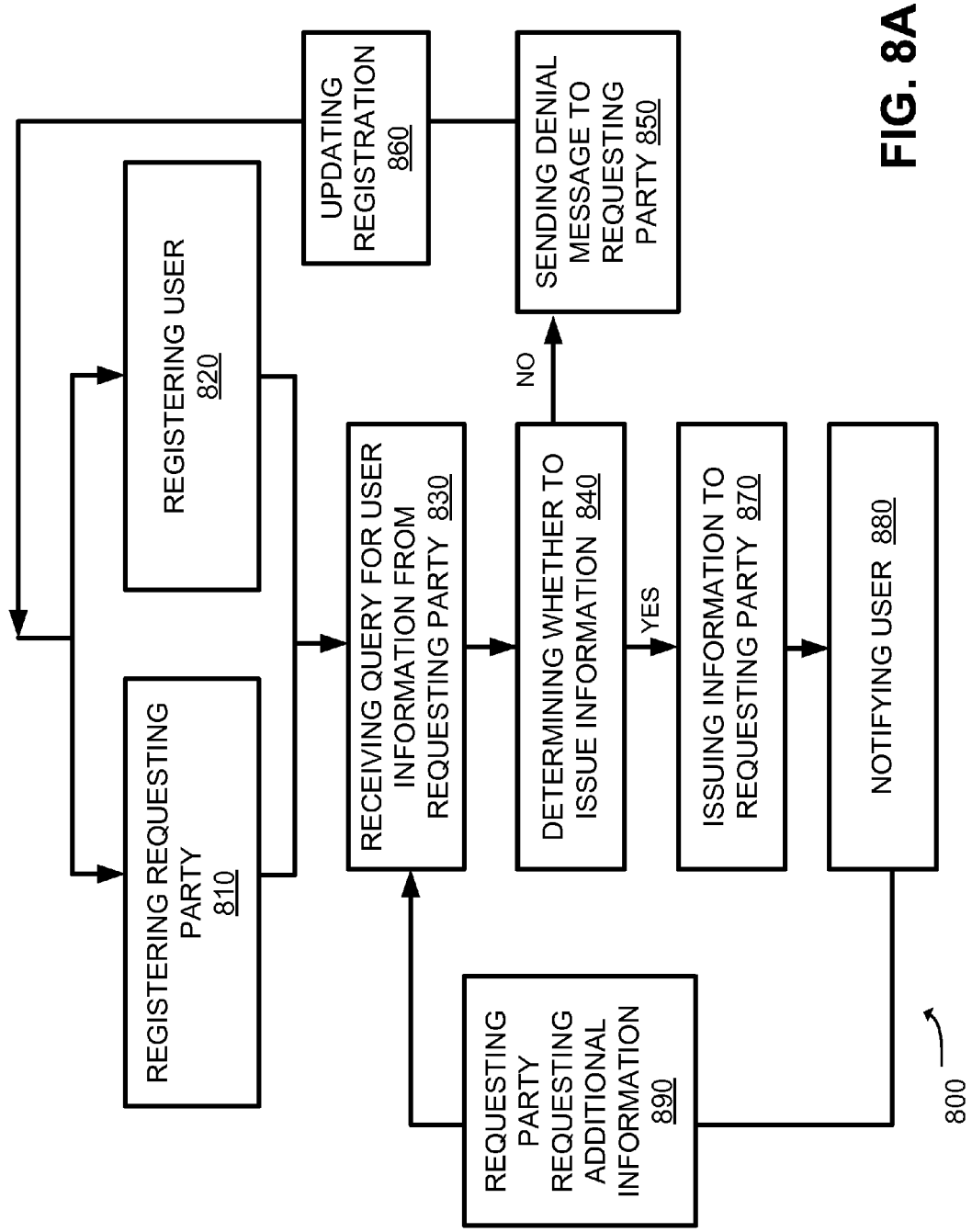

As depicted in FIG. 8A, persona-based identity management process 800 may include registering of a requesting party, such as a user/entity associated with requesting device 130 (block 810). Process block 810 may include the process blocks depicted in FIG. 8B. As depicted in FIG. 8B, in one implementation, data requester registration interface component 330 may, for example, receive information from the requesting party (block 811). Data requester registration interface component 330 may authenticate the requesting party based upon verifying the received information (block 812). For example, data requester registration interface component 330 may perform electronic verification of the provided information. It should be appreciated, however, that other known authentication techniques may be employed by data requester registration interface component 330 to authenticate the requesting party.

Still referring to FIG. 8B, as part of the registering of the requesting party (block 810), data requester registration interface component 330 may classify the requesting party into one or more categories (block 813). The categories may be based on a predicted or defined relationship between the authenticated user providing the data and the authenticated data requester. For example, data requester registration interface component 330 may classify the requesting party based on an analysis of information provided by the user/entity during the registration. For example, data requester registration interface component 330 may discern relationships between the requesting party and a data providing user. Furthermore, data requester registration interface component 330 may forward credential to the verified requesting party (block 814), such as unique encryption codes or credentials to enable the verified requesting party to establish a secure session or other connection to request and access stored persona-related information, as described below.

As depicted in FIG. 8A, persona-based identity management process 800 may also include registering a user (block 820). Process block 820 may include the process blocks depicted in FIG. 8C. As depicted in FIG. 8C, in one implementation, data provider registration interface component 310 may, for example, receive information from a user, such as a user associated with user device 120 (block 821). Data provider registration interface component 310 may authenticate the user based on the received information (block 822). For example, data provider registration interface component 310 may receive information to identify the user and to verify the user's identity using this identifying information. Various types of authentications may be used by data provider registration interface component 310. For example, data provided registration interface component 310 may perform electronic verification of the provided information. It should be appreciated, however, that other known authentication techniques may be employed by data provider registration interface component 310 to authenticate the user. Furthermore, data provider registration interface component 310 may provide the authenticated data providing user with data, such as unique encryption codes or credentials for establishing a secure session or other connection to, for example, personal data collection and access system 110 (block 823).

Data collection interface component 320 may provide to an authenticated user, such as to user device 120, one or more forms to collect data from the user (block 824). As described above, data collection interface component 320 may store the forms or may receive the forms may from a device associated with a requesting party or from another source. When providing the forms to the authenticated user, data collection interface component 320 may pre-populate the forms with previously collected and/or stored data associated with user, such as data acquired from other forms or the information provided by the user to data provider registration interface component 310. Data collection interface component 320 may collect personal information from the user (block 825), such as to collect the user's response to the forms.

Data collection interface component 320 may organize the data collected from the authenticated user to define multiple personas (block 826). Data collection interface component 320 may associate information from the user's collected data with the personas, for example, based on inputs from the user. Data collection interface component 320 may also organize data from the authenticated user into personas based on one or more forms from which the data was collected. Data collection interface component 320 may also organize data from the user may into personas based on inputs received from a requesting party. For instance, a requesting party can specify data collected from the user, and data collection interface component 320 can organize the requested data to form a persona directed to the requesting party.

Although the above discussion describes data being received from a user with whom the data is associated, it should be appreciated that information can be received from a third party identified by the user. For example, the user, who is a patient, can request that data collection interface component 320 collect information from the user's doctor, who would receive and respond to the data request forms instead of the user.

Continuing with FIG. 8A, persona-based identity management process 800 may further include receiving a query from a requesting party to access the personal information such as data collected from the user (block 830). In response to receiving the query, data access interface component 340 may determine whether to issue the information requested in the query (block 840).

Process block 840 may include the process blocks depicted in FIG. 8D. Referring now to FIG. 8D, the query is processed to identify a user and/or a requesting party associated with the query (block 841). For example, the requesting party may include, in the query, credentials associated with the data requester (e.g., assigned by data requester registration interface component 330) and/or the data provider (e.g., assigned by data provider registration interface component 310) to access one or more personas. An authenticated data requester may access information associated with user in response that authenticated data requester presenting encryption credentials associated with the data provider. Furthermore, a classification associated with the authenticated requesting party may be identified (block 842), a user persona associated with the query may be identified (block 843), and a determination is made regarding whether to provide the requested information based on a comparison of the identify requesting party classification and the identified persona (block 844).

In another implementation, the registered requesting party can access certain personas (such as anonymous persona 600e) without authorization from the user. For example, the requesting party can include a researcher who is collecting information about users without collecting information that could be used to identify the user. The requesting partying collecting the anonymous information may include, for example, a researching collecting information about the user's consumer behavior or information about the user's healthcare.

Continuing with FIG. 8A, if it is determined to deny the requesting party's query to access the requested information, such as when the requesting party's classification is not eligible to receive the user's persona associated with the data included in the query, a denial message may be sent to the requesting party (block 850). The requesting party can update its classification, for example, by providing addition/different registration information, and the query can be re-processed based on the updated classification (block 860). Alternatively, the data providing user may provide instructions to modify the persona or the modify access to the personas or the data requester may modify the query.

If it is determined to grant the requesting party's query to access the requested information (e.g., the classification of the requesting party's is eligible to access the user's persona associated with the requested information, the requested information may be issued to the requesting party (block 870). In one implementation, the registered user may be notified, for example, of access, by the requesting party, to the user's personal data (block 880). In response to accessing the information, the requesting party may update the query and/or request additional personal information from the user (block 890).

The foregoing description of implementations, described above, provides illustration and description, but is not intended to be exhaustive or to limit the present disclosure to the precise form disclosed. Modifications and variations are possible in light of the above teachings or may be acquired from practice of the disclosed embodiments.

For example, while series of blocks have been described with regard to FIGS. 8A-8D, the order of the blocks may be modified in other implementations. Further, non-dependent blocks may be performed in parallel.

Also, certain portions of the implementations may have been described as a "component" or "interface" that performs one or more functions. The terms "component" and "interface" may include hardware, such as a processor, an ASIC, or a FPGA, or a combination of hardware and software (e.g., software running on a processor).

It will be apparent that aspects described herein may be implemented in many different forms of software, firmware, and hardware in the implementations illustrated in the figures. The actual software code or specialized control hardware used to implement aspects does not limit the embodiments. Thus, the operation and behavior of the aspects were described without reference to the specific software code—it being understood that software and control hardware can be designed to implement the aspects based on the description herein.

Even though particular combinations of features are recited in the claims and/or disclosed in the specification, these combinations are not intended to limit the disclosure of the presented embodiments. In fact, many of these features may be combined in ways not specifically recited in the claims and/or disclosed in the specification.

No element, act, or instruction used in the present application should be construed as critical or essential to the disclosed embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method, comprising:
receiving, by a computer device, personal data associated with a user from a user device, wherein the user has a plurality of personas, and wherein each of the plurality of personas corresponds to at least one of a plurality of requester classifications;
associating, by the computer device, the received personal data with at least one of the plurality of personas;
storing, by the computer device, the received personal data with the associated at least one of the plurality of personas;
identifying, by the computer device, one or more of the plurality of requester classifications that correspond to the at least one of the plurality of personas associated with received personal data;
receiving, by the computer device and from a data requester, a query including a request for the personal data;
associating, by the computer device, the data requester with a requester classification, of
the plurality of requester classifications;
comparing, by the computer device, the requester classification associated with the data requester to the identified one or more of the plurality of requester classifications associated with received personal data; and sending, by the computer device and to the data requester, a message including the personal data in response to the requester classification of the data requester corresponding to the identified one or more of the plurality of requester classifications.

2. The method of claim 1, further comprising:
receiving, from the user device, a plurality of user information; and
forming the plurality of personas based on the received plurality of user information.

3. The method of claim 2, further comprising:
sending, to the user, one or more forms requesting the plurality of user information.

4. The method of claim 3, where each of the one or more forms is associated with at least one of the plurality of personas.

5. The method of claim 3, where one form, of the one or more forms, is sent to the computer device by the data requester.

6. The method of claim 1, further comprising:
receiving information from the data requester,
where associating the data requester with the requester classification is based on the received information from the data requester.

7. The method of claim 1, further comprising:
providing, by the computer device and to the user device, an authentication code; and
determining whether the query further includes the authentication code,
wherein sending the message including the personal data is further in response to determining that the query includes the authentication code.

8. An apparatus, comprising:
a memory to store instructions; and
a processor to execute the instructions to:
  receive information from at least one of a user or a data requester device
  verify the received information from the at least one of the user or the data requester device,
    provide a verification code to the at least one of the user or the data requester device in response to verifying the received information,
  receive, from the data requester device, a query from a first party including a request for personal data associated with the user, wherein the user differs from the first party,
  associate the first party with a requester classification,
  identify one or more personas, of a plurality of personas associated with the user, that correspond to the personal data requested in the query, and
  determine whether to grant the first party with access to the personal data based on the requester classification associated with the first party and the identified one or more personas.

9. The apparatus of claim 8, wherein the personal data includes a network address identifying a location where information associated with the user is stored, and wherein the processor, when granting the data requester device with access to the personal data, is further configured to send information identifying the network address to the data requester device.

10. The apparatus of claim 8, where the processor is further to:
provide forms that request personal information associated with the user;
collect the personal information requested in the forms; and
sort the personal information into the plurality of personas based on the forms.

11. The apparatus of claim 10, wherein the processor is further to:
receive one or more of the forms from the data requester device; and
determine to grant the first party with the access to the personal data when the personal data is requested in the one or more of the forms received from the data requester device.

12. The apparatus of claim 11, where the processor is further to:
automatically populate one of the forms with corresponding information collected in another one of the forms.

13. The apparatus of claim 8, wherein the processor is further to:
determine to grant the first party with the access to the personal data when the query includes the verification code.

14. The apparatus of claim 8, wherein the processor is further to:
identify one or more of a plurality of requester classifications that correspond to the one or more personas associated with the personal data; and
determine to grant the first party with the access to the personal data when the requester classification, associated with the first party, corresponds to the identified one or more of the plurality of personas.

15. The apparatus of claim 8, where the one or more personas associated with the user includes an anonymous persona that includes the requested personal data but does not include information that identifies the user.

16. A non-transient computer-readable medium storing instructions executable by a processor, non-transient computer-readable medium comprising:
one or more instructions to receive information from at least one of a user or a data requester, wherein the user and the data requester are different parties;
one or more instructions to verify the received information;
one or more instructions to provide a verification code to the least one of the user or the data requester in response to verifying the received information;
one or more instructions to receive, from the data requester, a query including a request for personal data associated with the user;
one or more instructions to associate the data requester with a requester classification,
one or more instructions to identify one or more personas, of a plurality of personas associated with the user, that correspond to the personal data requested in the query; and
one or more instructions to determine whether to grant the data requester with access to the personal data based on the requester classification associated with the data requester, the identified one or more personas, and whether the query includes the verification code.

17. The non-transient computer-readable medium of claim 16, further comprising:
one or more instructions to provide forms that request personal information associated with the user, where one of the forms is received from the data requester;
one or more instructions to automatically populate one of the forms with corresponding information collected in another one of the forms;

one or more instructions to collect the personal information requested in the forms;
one or more instructions to form the plurality of personas based on the collected personal information; and
one or more instructions to determine to grant the data requester with the access to the personal data in response to determining that the personal data is requested from the user in the form received from the data requester.

18. The non-transient computer-readable medium of claim 16, further comprising:
one or more instructions to notify the user when granting the data requester with the access to the personal data.

19. The non-transient computer-readable medium of claim 16, further comprising:
one or more instructions to access the information from at least one of the user or the data requester from a third party who differs from the user and the data requester.

* * * * *